(12) United States Patent
Welch

(10) Patent No.: US 11,464,657 B2
(45) Date of Patent: Oct. 11, 2022

(54) STENT AND METHOD OF MANUFACTURE

(71) Applicant: Tré Raymond Welch, Dallas, TX (US)

(72) Inventor: Tré Raymond Welch, Dallas, TX (US)

(*) Notice: Subject to any disclaimer, the term of this patent is extended or adjusted under 35 U.S.C. 154(b) by 0 days.

(21) Appl. No.: 16/951,878

(22) Filed: Nov. 18, 2020

(65) Prior Publication Data

US 2021/0154032 A1     May 27, 2021

Related U.S. Application Data

(60) Provisional application No. 62/939,064, filed on Nov. 22, 2019.

(51) Int. Cl.
| | |
|---|---|
| *A61F 2/88* | (2006.01) |
| *A61F 2/90* | (2013.01) |
| *A61L 31/04* | (2006.01) |
| *A61L 31/18* | (2006.01) |
| *A61F 2/82* | (2013.01) |

(52) U.S. Cl.
CPC ............... *A61F 2/885* (2013.01); *A61F 2/82* (2013.01); *A61F 2/90* (2013.01); *A61L 31/041* (2013.01); *A61L 31/18* (2013.01); *A61F 2250/001* (2013.01); *A61F 2250/0067* (2013.01); *A61F 2250/0098* (2013.01)

(58) Field of Classification Search
CPC .... A61F 2/885; A61F 2/82; A61F 2/90; A61F 2250/001; A61F 2250/0067; A61F 2250/0098; A61L 31/18
See application file for complete search history.

(56) References Cited

U.S. PATENT DOCUMENTS

| | | | |
|---|---|---|---|
| 4,800,882 | A | 1/1989 | Gianturco |
| 4,969,458 | A | 11/1990 | Wiktor |
| 5,603,722 | A | 2/1997 | Phan et al. |
| 5,607,445 | A | 3/1997 | Summers |
| 5,632,771 | A | 5/1997 | Boatman et al. |
| 5,716,410 | A | 2/1998 | Wang et al. |
| 5,762,625 | A | 6/1998 | Igaki |
| 5,782,907 | A | 7/1998 | Frantzen et al. |
| 6,063,111 | A | 5/2000 | Hieshima et al. |
| 6,666,881 | B1 | 12/2003 | Richter et al. |
| 6,692,521 | B2 | 2/2004 | Pinchasik |
| 7,128,755 | B2 | 10/2006 | Su et al. |

(Continued)

FOREIGN PATENT DOCUMENTS

EP     2644170 A1     10/2013

OTHER PUBLICATIONS

Agrawal, C.M. et al., Evaluation of poly(L-lactic acid) as a Material for Intravascular Polymeric Stents; Biomaterials; vol. 13; No. 3; pp. 176-182; 1992.

(Continued)

*Primary Examiner* — Dinah Baria
(74) *Attorney, Agent, or Firm* — Hitchcock Evert, LLP

(57) ABSTRACT

A dual opposing helical stent having a furled, small-diameter state and an expanded, large-diameter state. In the furled, small-diameter state, the stent includes a plurality of central lobes arranged at spaced-apart intervals and extending longitudinally defining a stent axis. The stent also includes peripheral lobes formed on the plurality of central lobes. The terminal ends of the stent are welded in a middle section of the stent. A method and technique for manufacturing the stent is also disclosed.

14 Claims, 6 Drawing Sheets

(56) References Cited

U.S. PATENT DOCUMENTS

| | | |
|---|---|---|
| 7,344,559 B2 | 3/2008 | Gray et al. |
| 7,412,993 B2 | 8/2008 | Tzeng |
| 9,155,640 B2 | 10/2015 | Welch |
| 9,480,586 B2 | 11/2016 | Welch |
| 9,943,423 B2 | 4/2018 | Welch |
| 10,786,373 B2 | 9/2020 | Welch |
| 2001/0000798 A1 | 5/2001 | Denardo |
| 2003/0114916 A1 | 6/2003 | Pinchasik |
| 2004/0098102 A1 | 5/2004 | Richter et al. |
| 2004/0193246 A1 | 9/2004 | Ferrera |
| 2005/0049683 A1 | 3/2005 | Gray et al. |
| 2005/0049684 A1 | 3/2005 | Gray et al. |
| 2005/0049685 A1 | 3/2005 | Gray et al. |
| 2005/0049686 A1 | 3/2005 | Gray et al. |
| 2005/0049688 A1 | 3/2005 | Gray et al. |
| 2005/0090888 A1 | 4/2005 | Hines et al. |
| 2005/0125053 A1 | 6/2005 | Yachia et al. |
| 2005/0203610 A1 | 9/2005 | Tzeng |
| 2005/0278019 A1 | 12/2005 | Gregorich |
| 2006/0058867 A1 | 3/2006 | Thistle et al. |
| 2007/0219619 A1 | 9/2007 | Dieck et al. |
| 2007/0282428 A1 | 12/2007 | Igaki |
| 2008/0071357 A1 | 3/2008 | Girton et al. |
| 2008/0077222 A1 | 3/2008 | Johnson et al. |
| 2008/0103584 A1 | 5/2008 | Su et al. |
| 2008/0221670 A1 | 9/2008 | Clerc et al. |
| 2010/0262227 A1 | 10/2010 | Rangwala |
| 2011/0106236 A1 | 5/2011 | Su et al. |
| 2011/0118822 A1 | 5/2011 | Welch |
| 2013/0245745 A1 | 9/2013 | Vong et al. |
| 2013/0261733 A1* | 10/2013 | Su .......................... A61F 2/88 623/1.15 |
| 2016/0008150 A1 | 1/2016 | Welch |
| 2017/0020699 A1 | 1/2017 | Welch |
| 2018/0193176 A1 | 7/2018 | Welch |

OTHER PUBLICATIONS

Grabow, Niels et al.; Mechanical properties of Laser Cut Poly(L-Lactide) Micro-Specimens: Implications for Stent Design, Manufacture and Sterilization; Journal of Biomedical Engineering; vol. 127; pp. 25-31; Feb. 2005.

Migliavacca, Francesco et al.; A Predictive Study of the Mechanical Behaviour of Coronary Stents by Computer Modelling; Medical Engineering & Physics; vol. 27; pp. 13-18; 2005.

Sullivan, Timothy M. et al.; Effect of Endovascular Stent Strut Geometry on Vascular Injury, Myointimal Hyperplasia, and Restenosis; Journal of Vascular Surgery; vol. 36; pp. 143-149; 2002.

Serruys, Patrick W. et al.; Coronary-Artery Stents; The New England Journal of Medicine; vol. 354; pp. 483-495; Feb. 2, 2006.

Topol, Eric J., Textbook of Interventional Cardiology; 4th Edition; Chapter 28; pp. 591-630; 2003.

Turner II, J.F. et al.; Characterization of Drawn and Undrawn Poly-L-Lactide Films by Differential Scanning Calorimetry; Journal of Thermal Analysis and Calorimetry; vol. 75; pp. 257-268; 2004.

Weir, N.A. et al., Processing, annealing and sterilisation of poly-L-lactide; Biomaterials; vol. 25; pp. 3939-3949 2004.

Welch, Tre' R.; Vascular Stent Analysis; Presentation to the Faculty of the Graduate School of the University of Texas at Arlington in Partial Fulfillment of the Requirements for the Degree of Master of Science in Biomedical Engineering; Aug. 2005.

Welch, Tre et al.; Analysis of the Deformation During Expansion of a Bioresorbable Fiber-Based Stent; BMES Annual Conference; Poster; Oct. 2006.

Welch, Tre et al.; Thermal Treatment Effects on a PLLA Bioresorbable Stent; ASME Summer Bioengineering Conference; Presentation; pp. 1-24; Jun. 2007.

Welch, Tre et al.; Influence of Thermal Annealing on the Mechanical Characteristics of a Resorbable PLLA Stent; BMES Annual Conference; Poster; Sep. 2007.

Welch, Tre et al.; Influence of Thermal Annealing on the Mechanical Characteristics of a Resorbable PLLA Stent; Southern Bioengineering Conference; Presentation; pp. 1-24; 2008.

Welch, Tre et al.; Characterizing the Expansive Deformation of Bioresorbable Polymer Fiber Stent; Annals of Biomedical Engineering; vol. 36; No. 5; pp. 742-751; May 2008.

Welch, Tre et al.; Thermal Treatment Improves Functional Characteristics of a PLLA Fiber Stent; BMES Annual Conference; Poster; Oct. 2008.

Welch, Tre R. et al.; The Influence of Thermal Treatment on the Mechanical Characteristics of a PLLA Coiled Stent; Journal of Biomedical Materials Research Part B: Applied Biomaterials; vol. 908; pp. 302-311; 2009 (published online Dec. 9, 2008 (www.interscience.wiley.com)).

Welch, Tre et al.; Range of Thermal Treatment upon the Mechanical Characteristics of PLLA Coiled Stents; ASME Summer Bioengineering Conference; Poster; Jun. 2009.

Welch, Tre et al; Thermal Treatment Effects Upon the Degradation Characteristics of a Bioresorbable PLLA Fiber Stent; ASME Summer Bioengineering Conference; Poster; Jun. 15, 2009.

Welch, Tre et al.; Novel Bioresorbable Stent Design and Fabrication: Congenital Heart Disease Applications Cardiovascular Engineering and Technology; vol. 4; No. 2; pp. 171-182; Jun. 2013.

Reddy, Surendranath R. Veeram et al.; A Novel Biodegradable Stent Applicable for Use in Congenital Heart Disease: Bench Testing and Feasibility Results in a Rabbit Model; Catheterization and Cardiovascular Interventions pp. 448-456; 2014.

Reddy, Surendranath R. Veeram et al.; A Novel Design Biodegradable Stent for Use in Congenital Heart Disease: Mid-Term Results in Rabbit Descending Aorta; Catheterization and Cardiovascular Interventions; 2014.

Herbert, Carrie E. et al.; Bench and Initial Preclinical Results of a Novel 8 mm Diameter Double Opposed Helical Biodegradable Stent; Catheterization and Cardiovascular Interventions; pp. 902-911; 2016.

* cited by examiner

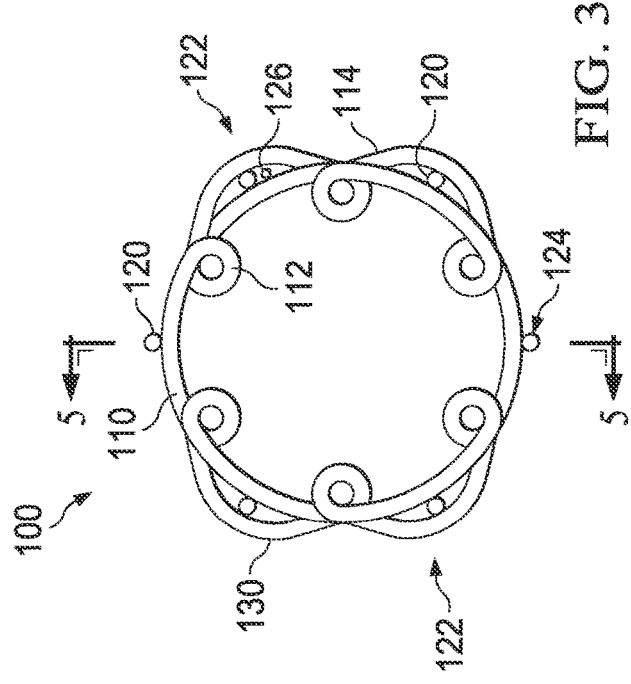
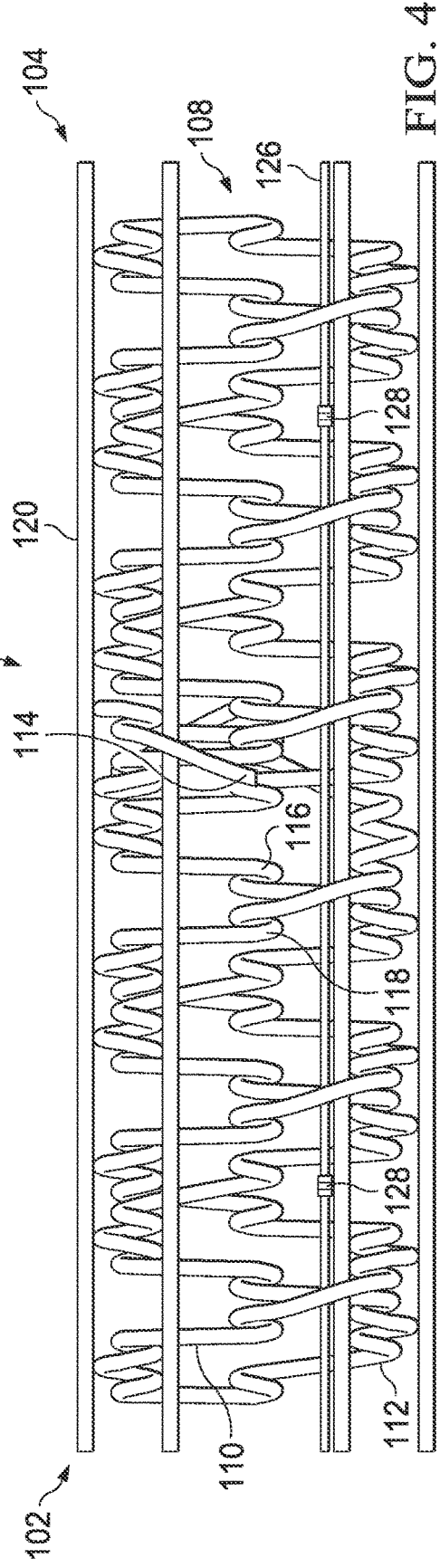

STENT AND METHOD OF MANUFACTURE

CROSS-REFERENCE TO RELATED APPLICATION

This application claims the benefit of priority from U.S. Provisional Application No. 62/939,064 filed on Nov. 22, 2019, which is incorporated herein by reference.

FIELD OF THE DISCLOSURE

The invention relates generally to stents, including expandable stents for vascular systems.

BACKGROUND

Stents are used for treating various types of vascular conditions. A stent can be implanted within a vessel in a small configuration using a delivery catheter or balloon and then expanded to a larger size against the walls of the vessel.

Stents can be metallic or non-metallic with different characteristics tied to design choices. Stents may have a furled state—small-diameter configuration—and an unfurled state—large-diameter configuration. The stent may be deployed in the furled state then expanded to the unfurled state for implementation.

Non-metallic stents having central coils and peripheral coils in a furled state are disclosed in U.S. Provisional Application No. 61/261,486 entitled "Stent and Method for Fabrication Thereof" and the patents and applications related thereto, including U.S. Pat. Nos. 9,155,640, 9,480, 586, 9,943,423 and U.S. Patent Publication No. 2018/0193176, which are all incorporated herein by reference.

As stent sizes increase for use in larger vessels, the mechanical characteristics and stresses on the stent change. In addition, the deployment may require larger changes between the diameter of the furled state and the diameter of the unfurled state, which cause further stresses on existing stent designs.

Stents may be created by winding the selected material from one end to the other. When creating peripheral lobes, the material may be wound on a mandrel, wherein the central lobes and the peripheral lobes are created as the material is wound. In Poly-L-Lactic Acid (PLLA) stents, the terminal ends of a wound PLLA element are welded at the ends. For example, a terminal end of the PLLA element may be welded to the adjacent central coil at the end of the stent.

The abovementioned family of patents and applications teaches dual opposing helical stents with peripheral lobes. These stents may be created by winding a PLLA element in a rotational direction to form central and peripheral lobes as it moves along the length of the stent. At the second end, the PLLA element continues to be wound in the same rotational direction to create another set of central and peripheral lobes as the element moves longitudinally back to the starting end. Both terminal ends of the PLLA element may be welded to adjacent central lobes or each other.

These stents provide mechanical integrity by withstanding axial compression from the vessel's walls and adhere well to prevent stent migration. The mechanical integrity may be compromised if the welds for the terminal ends fail. As the size of a stent increases, the stent is deployed on a larger balloon, which often increases to a larger size faster than smaller stents. This expansion can cause the terminal end welds to fail, which can lead to additional weld failures along the stent. For instance, 6 millimeter diameter and larger stents are more likely to have terminal end welds fail during expansion than smaller stent sizes. These weld ruptures can lead to stents being axially compressed and a complete failure of a stent.

SUMMARY

The present disclosure provides a stent configured to maintain mechanical integrity as the diameters of stents increase and stents expand more quickly.

In some embodiments, the stent includes a dual opposing helical pattern with terminal ends around the center of the stent. The dual opposing helical pattern includes a plurality of central lobes spaced longitudinally along the stent. Each central lobe may have one or more peripheral lobes. Peripheral lobes may be directed inward towards the center of the stent in some embodiments. In other embodiments, the peripheral lobes may lie in a cylindrical plane of the stent—i.e. in a surface of a cylindrical shape or the shape of a tube.

The stent may include one or more longitudinal rods extending along the length of the stent. In some embodiments, the longitudinal rods are connected to the central lobes between peripheral lobes.

In some embodiments, each terminal end is welded to a central lobe in a middle section of the stent. Longitudinal rods may also be welded to the lobes of the stent. In addition, some portions of central lobes may be welded together at a point in which they intersect.

In some embodiments, the stent is made by winding a PLLA element around a mandrel in a rotational direction. The winding may begin at one end with an unwound section of the PLLA element remaining at the first end. The PLLA element is wound forming central lobes and peripheral lobes extending longitudinally along the stent. At the second end, the PLLA element continues to be wound in the same rotational direction as the PLLA element is threaded back towards the first end of the stent. The back-winding brings the terminal end to a middle section of the stent. The unwound section of the stent is then wound in the opposite rotational direction from the first end to the middle section of the stent. The PLLA element is threaded to make additional central and peripheral coils as the element moves longitudinally toward the middle section.

In some embodiments, the process may begin in the middle section and proceed by winding in a rotational direction to the first end, then back to the second end and then proceed to the middle section. During this process, the same rotational winding direction may be used.

A BRIEF DESCRIPTION OF THE DRAWINGS

Embodiments will now be described, by way of example only, with references to the accompanying drawings in which:

FIG. 3 is an end view of an embodiment of a stent;

FIG. 4 is a side view of an embodiment of a stent;

DETAILED DESCRIPTION

Figure 1:
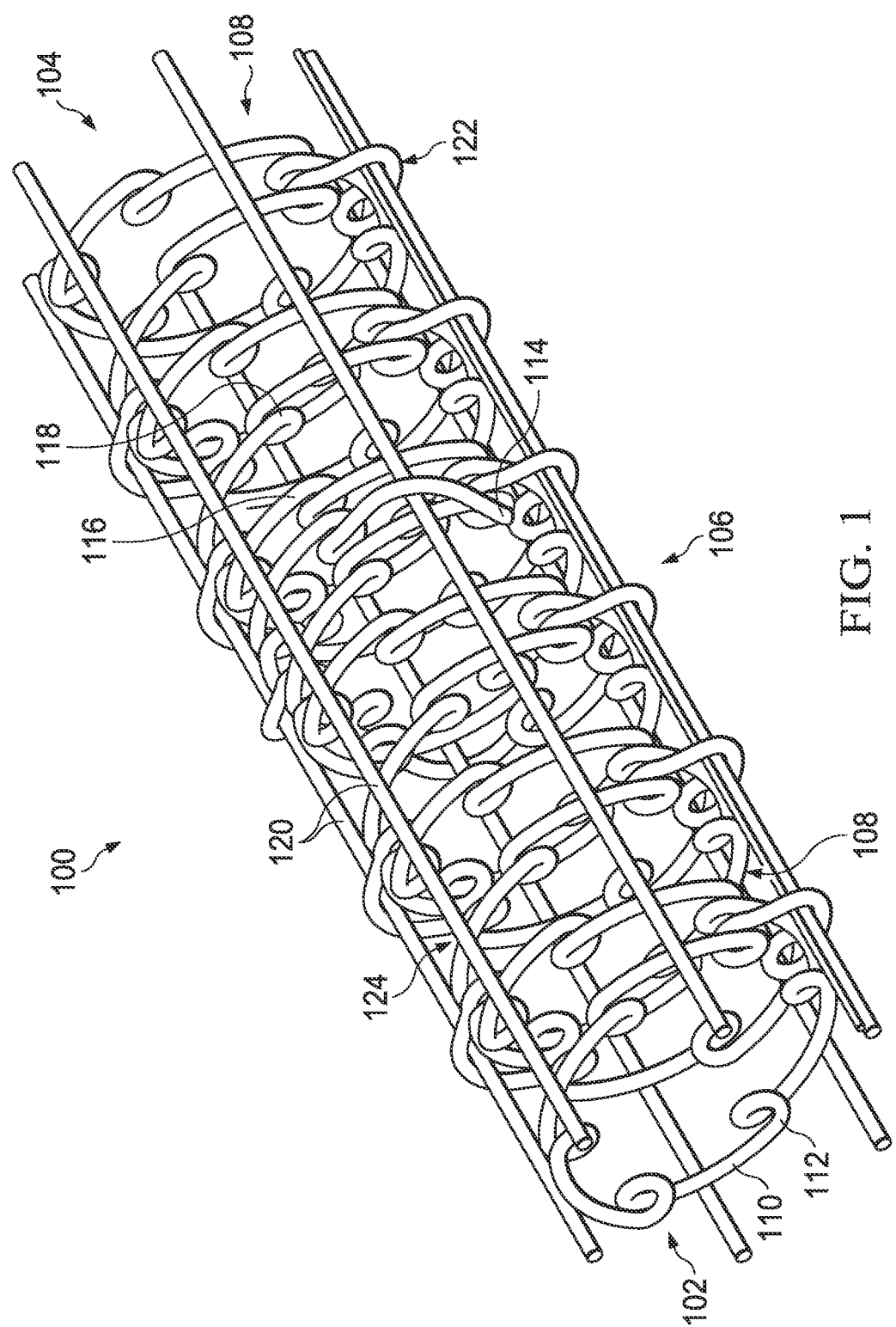
FIG. 1 is a perspective view of an embodiment of a stent.

While this invention may be embodied in many different forms, there will herein be described in detail preferred embodiments of the invention with the understanding that the present disclosure is to be considered as an exemplification of the principles of the invention and is not intended to limit the broad aspects of the invention to the embodiments illustrated. It will be understood that the invention may be embodied in other specific forms without departing from the spirit or central characteristics thereof. The present embodiments, therefore, are to be considered in all respects as illustrative and not restrictive, and the invention is not to be limited to the details given herein.

FIGS. 1 through 5 show views of an embodiment of stent 100 in a furled, small-diameter state; it should be understood that stent 100 is expandable to an unfurled, large-diameter state (e.g., by balloon catheter insertion and inflation/pressurization). The stent 100 extends from a first end 102 to a second end 104 and has a middle section 106 between ends 102 and 104. The stent 100 includes a longitudinal axis extending from the first end 102 to the second end 104.

Embodiments of stent 100 include an element 108 disposed in a coiled manner and extending in a longitudinal direction along the longitudinal axis between ends 102 and 104. Element 108 is coiled to form a number of central lobes 110 (e.g., each rotation of element 108 forms one lobe 110) and peripheral lobes 112 (e.g., smaller loops formed on central lobes 110).

In some embodiments, central lobes 110 are equally spaced along the longitudinal axis of stent 100 or have a uniform coil pitch along stent 100 (i.e., a uniform distance between each central lobe 110). However, it should be understood that the coil pitch may vary along one or more portions of stent 100.

Peripheral lobes 112 are formed by additional coils of element 108 during a coil rotation of a particular central lobe 110. In the embodiment illustrated in FIG. 1, each central lobe 110 includes six peripheral lobes 112. However, it should be understood that the quantity of peripheral lobes 112 formed along central lobes 110 may vary. Further, in FIG. 1, each central lobe 110 includes peripheral lobes 112. However, it should be understood that some central lobes 110 may be devoid of a peripheral lobe 112, or some central lobes 110 may include a greater or fewer quantity of peripheral lobes 112 than other central lobes 110. In some embodiments, the size and number of peripheral lobes 112 may vary.

The ends of element 108 are in the middle section 106 of the stent 100. In the perspective view shown in FIG. 1, terminal end 114 is located in the front, and terminal end 130 is not visible in the back. FIG. 2 shows a rotated, perspective view of terminal ends 114 and 130 of element 108.

In some embodiments, stent 100 comprises longitudinal support rods 120 extending longitudinally along stent 100. For example, in the embodiment illustrated in FIG. 1, stent 100 comprises six support rods 120; however, it should be understood that stent 100 may include a greater or fewer quantity of support rods 120. In some embodiments, rods 120 may be located at substantially equal distances from each other as measured about a circumference or cylindrical plane formed by central lobes 110. However, it should also be understood that rods 120 may be located at unequal distances relative to each other.

In some embodiments, element 108 and rods 120 may comprise a non-metallic material, such as a polymer fiber or multiple polymer fibers. For example, in some embodiments, element 108 and rods 120 may be formed from Poly-L-Lactic Acid (PLLA). However, it should be understood that other materials, such as a Poly-D,L-Lactide (PDLA) polymer or other polymer, may be used to form element 108 and rods 120. Rods 120 may be attached or otherwise secured to central lobes 110 using a variety of different methods or materials. For example, in some embodiments, rods 120 may be attached to central lobes 110 using a PLLA material (e.g., PLLA dissolved in chloroform) such that the PLLA mixture is used to glue or weld rods 120 to central lobes 110. In some embodiments, rods 120 may be ultrasonically welded to central lobes 110.

Rods 120 may be attached or otherwise secured to each successive central lobe 110 along the longitudinal length of stent 100 or may be intermittently attached to central lobes 110 as rod 120 extends along stent 100 (e.g., every other central lobe 110, every third central lobe 110, or at other uniform or non-uniform spacing intervals). Further, in some embodiments, rods 120 may be attached or otherwise secured to external sides of central lobes 110; however, it should be understood that rods 120 may be attached or otherwise secured to internal sides of central lobes 110. For example, in some embodiments, rods 120 may be woven or intermittently transition from an external location to an internal location of stent 100 relative to central lobes 110 as rods 120 extend along the longitudinal length of stent 100. For example, rod 120 may be secured to stent 100 by attaching rod 120 to an exterior surface of a first and second central lobe 110, to an interior surface of the third central lobe 110, to the exterior surface of the fourth and fifth central lobes, etc. Thus, rods 120 may weave inwardly and outwardly between interior and exterior areas of a stent 100 as rods 120 extend longitudinally according to a uniform or non-uniform pattern.

Figure 2:
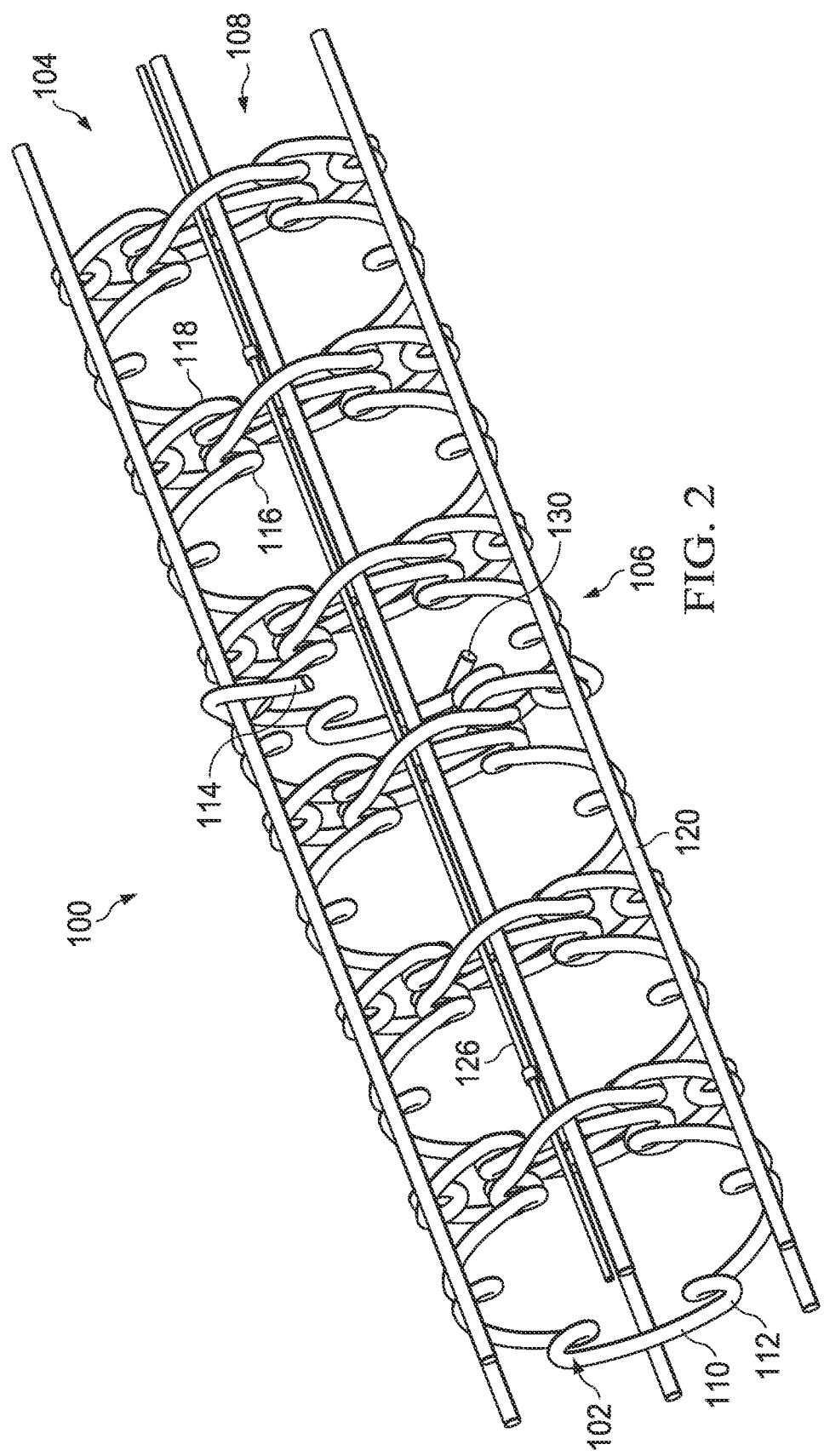
FIG. 2 is another perspective view of an embodiment of a stent.

FIGS. 1 and 2 show that four of the rods 120 are located on the outside of central lobes 110 (as indicated by reference 124) and two rods 120 are located on the inside of central lobes 110 (as indicated by reference 122). In addition, the element 108 passes over the rods 120 prior to the terminal ends 114 and 130.

FIG. 3 illustrates an end view from stent end 104. The end view of central lobes 110 with six peripheral lobes 112 shows rods 120 spaced around the stent 100. Some rods 120 are located on the outside surface of central lobes 110 (see 124) and others are on the inside surface of central lobes 110 (see 122). In addition, the overlap on the outside of rods 120 as the element approaches terminal ends 114 and 130 is also shown.

The side view in FIG. 4 shows that the stent 100 is formed as a dual opposing helical stent with terminal ends 114 and 130 in the middle section 106 of the stent 100. The opposing peripheral lobes 116 and 118 are illustrated in the perspective and side views of the stent 100. For illustration, opposing peripheral lobe 116 coils counter-clockwise from the direction of the first end 102 to the second end 104 and opposing peripheral lobe 118 coils clockwise from the direction of the first end 102 to the second end 104.

Figure 5:
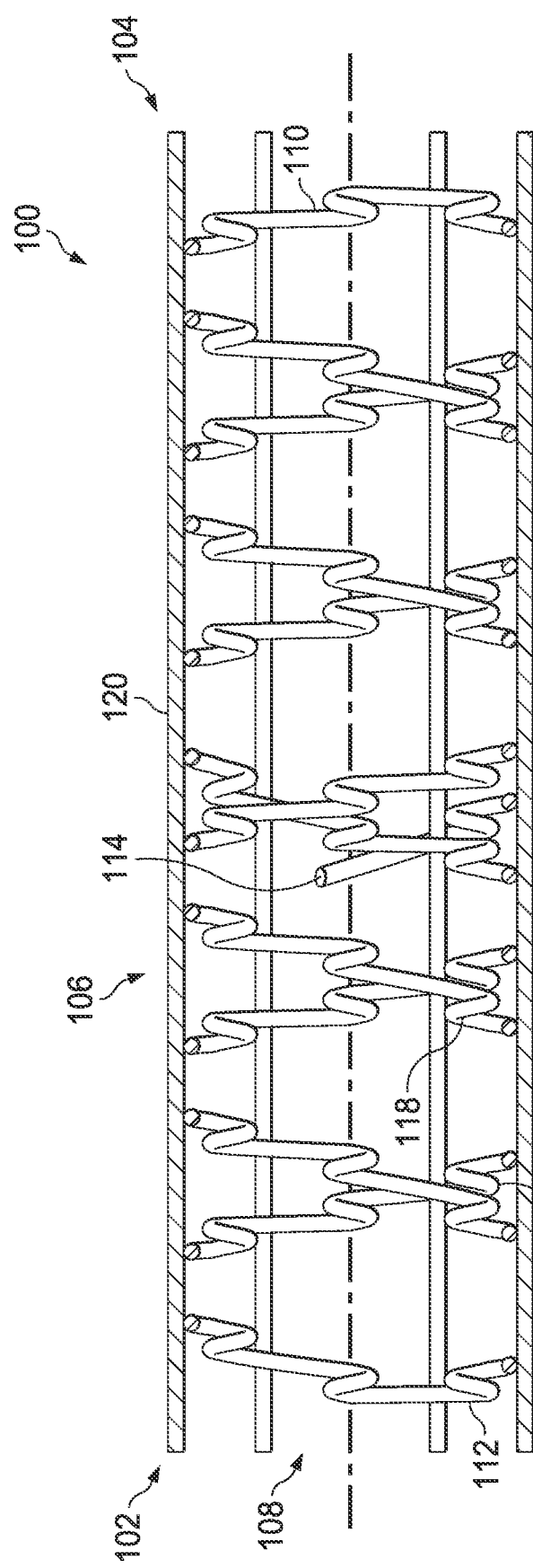
FIG. 5 is a cross-section view of an embodiment of a stent.

The cross-section view in FIG. 5 further illustrates the central lobes 110 with peripheral lobes 112 in the dual opposing helical stent 100. The stent 100 is oriented such that the terminal end 114 of element 108 is shown in the back of the middle section 106. On each end 102 and 104, the element 108 creates a central lobe 110 and winds back to the middle section 106.

In some embodiments, stent 100 may be formed by winding an element 108 to create central lobes 110 and peripheral lobes 112. The winding process may begin at the first end 102 with the terminal end 130 and a portion of the element 108 reserved. The unreserved portion of element 108 is wound around a mandrel in a first rotational direction (e.g., clockwise) creating central lobes 110 with peripheral lobes 112 in each central lobe 110. This winding continues until the element 108 reaches the second end 104. At the second end 104, the element 108 is back-wound in the first rotational direction, by threading it through the mandrel to create central lobes 110 and peripheral lobes 112 as it winds back to the middle section 106. In the middle section 106, the element 108 terminates with terminal end 114. Then, the reserved portion of element 108 is back-wound in a second rotational direction (e.g., counter-clockwise), threading through the mandrel to create additional central lobes 110 and peripheral lobes 112 until the element 108 reaches the middle section 106 and terminates with terminal end 114.

This creates a stent 100 with three sets of central lobes 110, each having peripheral lobes 112. The first set of central lobes 110 extends from the first end 102 to the second end 104. The second set of central lobes 110 extends from the second end 104 to the middle section 106, terminating with terminal end 114. The third set of central lobes 110 extends from the first end 102 to the middle section 106, terminating with terminal end 130.

In another embodiment, stent 100 may be created by winding an element 108 on a mandrel using the same rotational winding direction. The creator may start with terminal end 130 in the middle section 106 of the planned stent 100. The central lobes 110 and peripheral lobes 112 are created as the element is wound in a rotational direction from the middle section 106 to the first end 102. The process continues from the first end 102 by back-winding element 108 to create additional central lobes 110 and peripheral lobes 112 from the first end 102 to the second end 104. The back-winding process follows the same rotational winding direction as the element 108 is threaded through the first half of the stent 100 and wound from the middle section 106 to the second end 104. Finally, the element 108 is back-wound from the second end 104 to the middle section 106 threading around the second half of stent 100 until the terminal end 114 reaches the middle section 106.

The stent 100 may be deployed using a balloon catheter. The furled stent 100 is attached to the balloon catheter and inserted into the vascular system. When the balloon catheter is in place, the balloon is expanded to unfurl the stent 100 into the expanded state, which engages the vessel's walls. When the stent 100 expands, the middle section 106 may have an opening created by the winding pattern of the terminal ends 114 and 130.

The winding design in stent 100 alleviates stress at the welds for terminal ends 114 and 130. In addition, the fully coiled lobes at the ends 102 and 104 withstand the stress caused by the balloon expansion. Because the welds are not compromised, the stent 100 may be deployed in larger vessels without a heightened risk of stent failure that occurs when welds fail. The central welds for the terminal ends 114 and 130 remain significantly below the fail stress and yield stress levels.

When the stent 100 expands, the peripheral lobes 112 unfurl. In PLLA stents, the unfurled peripheral lobes 112 plasticize creating regions in the expanded stent 100 that are more rigid than other regions of the stent 100. The non-peripheral lobe regions continue to reflect the elasticity of the PLLA material. Together, these features provide a stent 100 with structural integrity and elastic recoil.

In some embodiments, a radio-opaque material may be used in stent 100 to enable x-ray and/or fluoroscopic identification of stent 100 during delivery or deployment. For example, in some embodiments, barium sulfate, water-soluble iodine and/or other materials may be laced or loaded into the polymer material used to form element 108 and rods 120. In some embodiments, a radio-opaque material may be mixed with a PLLA mixture (e.g., PLLA dissolved in chloroform), which is used to glue or weld rods 120 to central lobes 110. The PLLA and radio-opaque mixture provides fluoroscopic visibility of stent 100.

In some embodiments, a radio-opaque material may be attached to the stent 100, such as securing a radio-opaque metal (e.g., platinum) to rods 120 or element 108. The radio-opaque material may be attached using a PLLA material or other type of material. Further, in some embodiments, a radio-opaque sheath may be used with stent 100. For example, in some embodiments, a film comprised of a PLLA material loaded with a radio-opaque material is wrapped partially or entirely around stent 100 to enable x-ray and/or fluoroscopic identification of stent 100 during delivery or deployment. In some embodiments, the PLLA stent 100 may be loaded with drugs, such as curcumin and niacin.

The embodiment shown in FIGS. 1-4 includes an optional, additional fiber 126 adjacent to one of the rods 120. This fiber 126 may include the radio-opaque material or be loaded with an additional drug. FIG. 4 illustrates platinum coils 128 located at two locations along the additional fiber 126. These platinum coils 128 illustrate one option for securing radio-opaque materials to the stent 100.

In some embodiments, the stent 100 may be made of a Poly-D,L-Lactide (PDLA) polymer or include a PDLA fiber or rod. The PDLA fiber may be loaded with anti-inflammatory or anti-proliferative drugs, which are released over an extended time period. For example, the PDLA fiber may slowly release impregnated drugs over the course of two or three years. Stents 100 may include other similar polymers, such as polycaprolactone (PCL), Poly-lactide-co-glycolide (PLGA) and Polyglycolide (PGA), and polydioxanone (PDS), which can be made with anti-inflammatory drugs, anti-proliferative drugs such as sirolimus, antibiotics and other therapeutic agents.

Figure 6:
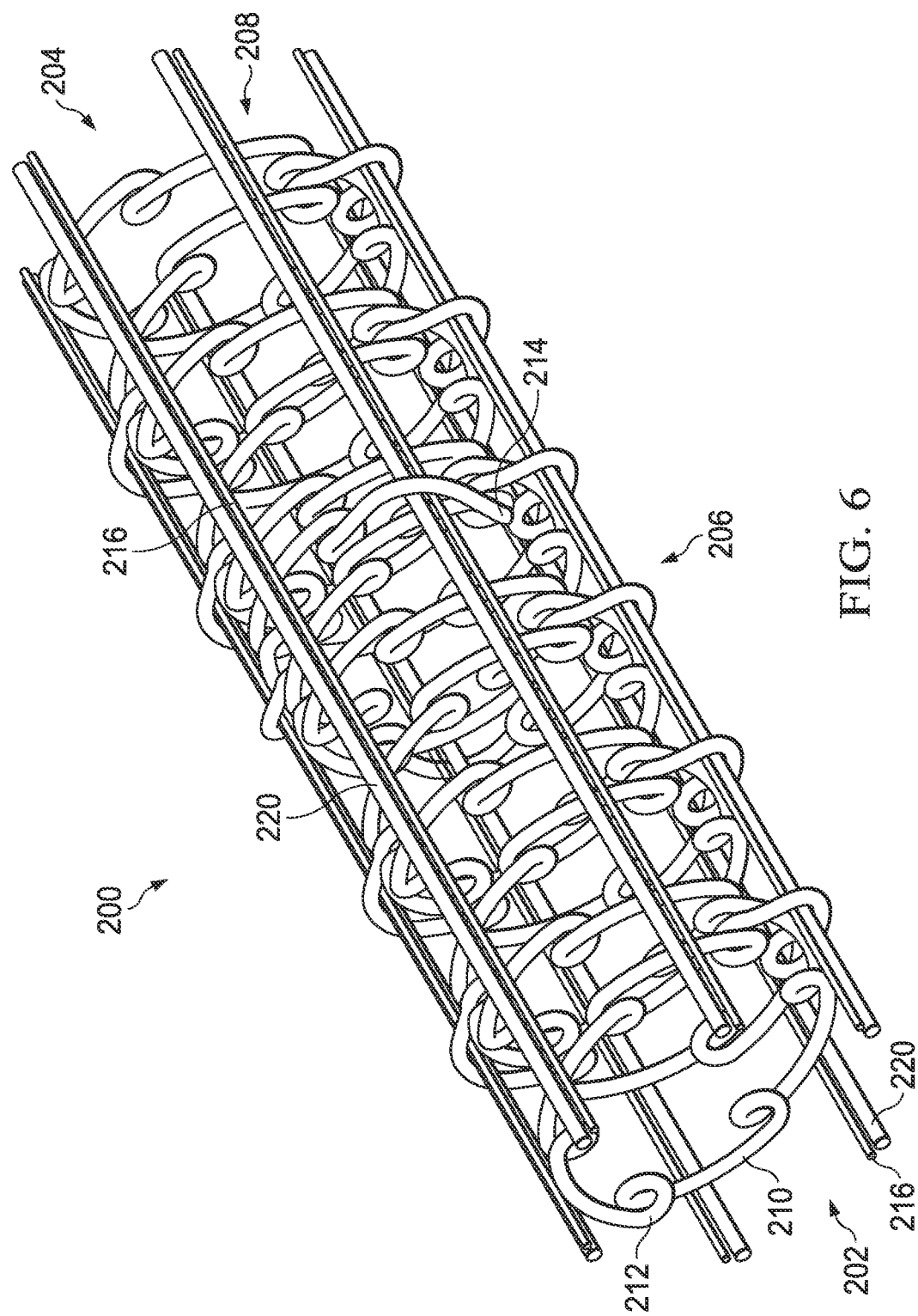
FIG. 6 is a perspective view of another embodiment of a stent.

FIG. 6 shows a perspective view of stent 200 in a furled, small-diameter state; it should be understood that stent 200 is expandable to an unfurled, large-diameter state (e.g., by balloon catheter insertion and inflation/pressurization). The stent 200 may be configured to expand to any diameter. For example, the stent 200 may be 6 mm, 7 mm, 8, mm, 10 mm, 12 mm, or any other stent diameter. The stent 200 extends from a first end 202 to a second end 204 and has a middle section 206 between ends 202 and 204. The stent 200 includes a longitudinal axis extending from the first end 202 to the second end 204.

Embodiments of stent 200 include an element 208 disposed in a coiled manner and extending in a longitudinal direction along the longitudinal axis between ends 202 and 204. Element 208 is coiled to form a number of central lobes 210 (e.g., each rotation of element 208 forms one lobe 210) and peripheral lobes 212 (e.g., smaller loops formed on central lobes 210). The ends of element 208 are in the middle section 206 of the stent 200. In the perspective view shown in FIG. 6, terminal end 214 is located in the front, and the second terminal end is located in the back (not shown).

In some embodiments, stent 200 comprises longitudinal support rods 220 extending longitudinally along stent 200. For example, stent 200 comprises six support rods 220; however, it should be understood that stent 200 may include a greater or fewer quantity of support rods 220. In some embodiments, rods 220 may be located at substantially equal distances from each other as measured about a circumference or cylindrical plane formed by central lobes 210. However, it should also be understood that rods 220 may be located at unequal distances relative to each other. In this embodiment, the stent 200 includes six additional drug eluding fibers 216, which are paired with support rods 220. The number of drug eluding fibers 216 may vary.

Figure 7:
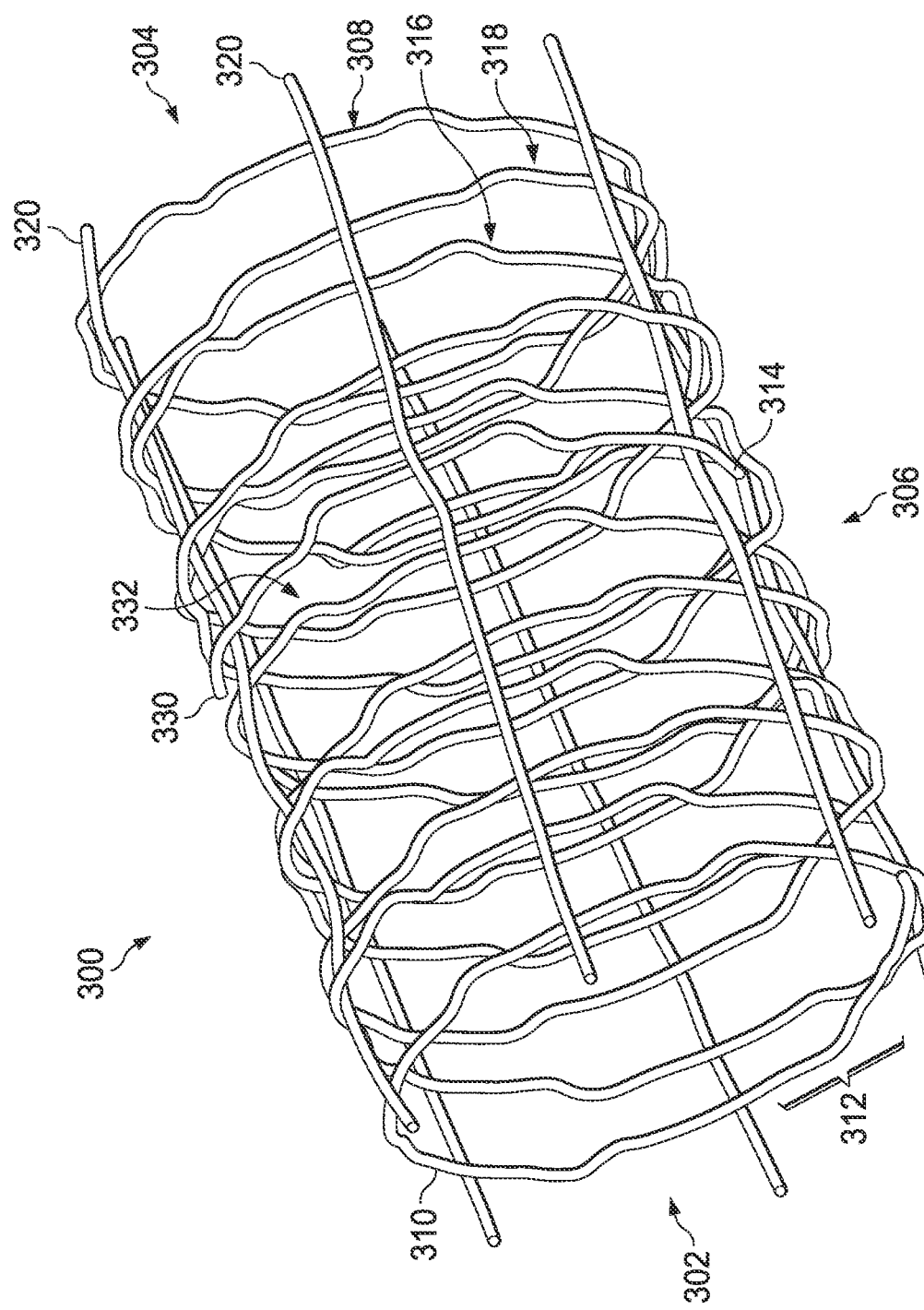
FIG. 7 is a perspective view of another embodiment of a stent.

FIG. 7 shows a perspective view of stent 300 in an unfurled, expanded state. It should be understood that stent 300 was expanded from a furled, small-diameter state (e.g., by balloon catheter insertion and inflation/pressurization) in a similar manner as the stents discussed above with central and peripheral lobes. The stent 300 extends from a first end 302 to a second end 304 and has a middle section 306 between ends 302 and 304. The stent 300 includes a longitudinal axis extending from the first end 302 to the second end 304.

Stent 300 includes an element 308 disposed in a coiled manner and extending in a longitudinal direction along the longitudinal axis between ends 302 and 304. The unfurled element 308 includes deformed peripheral lobe sections 312 between central lobe sections 310. The size of the stent 300 corresponds to the length of a central lobe and the peripheral lobes that were on that central lobe. The ends of element 308 are in the middle section 306 of the stent 300. In the perspective view shown in FIG. 7, terminal end 314 is located toward the bottom, and terminal end 330 is located near the top. The opposing windings create opening 332 near the terminal ends 314 and 330 of the element 308.

The peripheral lobe sections 312, created by deforming the peripheral lobes during expansion, plasticize creating additional rigidity in the implanted stent. While the peripheral lobe sections 312 are more rigid, the central lobe sections 310 maintain some flexibility. As such, the expanded stent 300 has both rigid and elastic characteristics that provide mechanical integrity to maintain form while also allowing some flex during times of natural stress caused in the vascular system by pressure against vessel walls and blood flow.

The stent 300 is an expanded state from a dual opposing helical stent. The expanded state of opposing peripheral lobes 316 and 318 are shown. The opposing peripheral lobe 316 was coiled counter-clockwise from the direction of the first end 302 to the second end 304 and opposing peripheral lobe 318 was coiled clockwise from the direction of the first end 302 to the second end 304.

In some embodiments, stent 300 comprises longitudinal support rods 320 extending longitudinally along stent 300. For example, stent 300 comprises six support rods 320; however, it should be understood that stent 300 may include a greater or fewer quantity of support rods 320. In some embodiments, support rods 320 may be located at substantially equal distances from each other as measured about a circumference or cylindrical plane formed by stent 300. However, it should also be understood that rods 320 may be located at unequal distances relative to each other. In some embodiments, the stent 300 may include additional drug eluding fibers, which are paired with support rods. The number of drug eluding fibers may vary.

The invention being thus described and further described in the claims, it will be obvious that the same may be varied in many ways. Such variations are not to be regarded as a departure from the spirit and scope of the invention, and all such modifications as would be obvious to one skilled in the art are intended to be included within the scope of the apparatus and method described.

The invention claimed is:

1. A stent having a furled, small-diameter state and an expanded, large-diameter state, the stent comprising, in the furled, small-diameter state:
 a polymer element coiled to form:
  a first plurality of central lobes arranged longitudinally along a stent axis from a first end to a second end of the stent,
  a second plurality of central lobes extending from a middle section of the stent to the first end of the stent,
  a third plurality of central lobes extending from the middle section of the stent to the second end of the stent, and
  at least one peripheral lobe on each of the first plurality of central lobes, the second plurality of central lobes and the third plurality of central lobes;
 wherein the polymer element rotates in a first rotational direction to form the first plurality of central lobes, and each of the first plurality of central lobes is spaced along the stent axis as the polymer element moves from the first end to the second end;
 wherein the polymer element rotates in a second rotational direction to form the second plurality of central lobes, and each of the second plurality of central lobes is spaced along the stent axis as the polymer element moves from the first end to the middle section;
 wherein the polymer element rotates in the first rotational direction to form the third plurality of central lobes, and each of the third plurality of central lobes is spaced along the stent axis as the polymer element moves from the second end to the middle section;
 wherein the second plurality of central lobes and the third plurality of central lobes form an opposing winding pattern to the first plurality of central lobes along the stent axis; and
 wherein the terminal ends of the polymer element are in the middle section.

2. The stent of claim 1, wherein the at least one peripheral lobe comprises a plurality of peripheral lobes disposed about each of the first plurality of central lobes, the second plurality of central lobes and the third plurality of central lobes.

3. The stent of claim 1, wherein the polymer element comprises at least one of a Poly-L-Lactic Acid fiber, a Poly-D,L-Lactide, a polycaprolactone fiber, a Poly-lactide-co-glycolide fiber, a Polyglycolide fiber or a polydioxanone fiber.

4. The stent of claim 1, wherein the polymer element comprises a polymer fiber loaded with a material.

5. The stent of claim 4, wherein the material is radio-opaque.

6. The stent of claim 4, wherein the material is a drug.

7. The stent of claim 4, wherein the material is at least one of curcumin, niacin, an anti-inflammatory material or anti-proliferative material.

8. A stent having a furled, small-diameter state and an expanded, large-diameter state, the stent comprising, in the furled, small-diameter state:
 a polymer element coiled to form:
  a first plurality of central lobes arranged longitudinally along a stent axis from a first end to a second end of the stent,
  a second plurality of central lobes extending from a middle section of the stent to the first end of the stent,
  a third plurality of central lobes extending from the middle section of the stent to the second end of the stent, and at least one peripheral lobe on each of the first plurality of central lobes, the second plurality of central lobes and the third plurality of central lobes;

wherein the second plurality of central lobes and the third plurality of central lobes form an opposing winding pattern to the first plurality of central lobes along the stent axis; and wherein the terminal ends of the polymer element are in the middle section.

9. The stent of claim 8, wherein the at least one peripheral lobe comprises a plurality of peripheral lobes disposed about each of the first plurality of central lobes, the second plurality of central lobes and the third plurality of central lobes.

10. The stent of claim 8, wherein the polymer element comprises at least one of a Poly-L-Lactic Acid fiber, a Poly-D,L-Lactide, a polycaprolactone fiber, a Poly-lactide-co-glycolide fiber, a Polyglycolide fiber or a polydioxanone fiber.

11. The stent of claim 8, wherein the polymer element comprises a polymer fiber loaded with a material.

12. The stent of claim 11, wherein the material is radio-opaque.

13. The stent of claim 11, wherein the material is a drug.

14. The stent of claim 11, wherein the material is at least one of curcumin, niacin, an anti-inflammatory material or anti-proliferative material.

* * * * *